United States Patent [19]

Cameron

[11] Patent Number: 5,342,320

[45] Date of Patent: Aug. 30, 1994

[54] HYPODERMIC SYRINGE HAVING SHIELDING TO PREVENT ACCIDENTAL INJURY FOLLOWING USE

[76] Inventor: Robert W. Cameron, 1333 Lincoln, Bellingham, Wash. 98226

[21] Appl. No.: 5,019

[22] Filed: Jan. 15, 1993

[51] Int. Cl.$^5$ .............................................. A61M 5/32
[52] U.S. Cl. ........................... 604/192; 604/198
[58] Field of Search ............... 604/192, 187, 198, 263, 604/199, 110

[56] References Cited

U.S. PATENT DOCUMENTS

| | | | |
|---|---|---|---|
| 4,416,663 | 11/1983 | Hall | 604/199 X |
| 4,863,434 | 9/1989 | Bayless | 604/198 |
| 4,909,792 | 3/1990 | Norelli | 604/192 |

*Primary Examiner*—John D. Yasko
*Attorney, Agent, or Firm*—Todd N. Hathaway

[57] ABSTRACT

A hypodermic syringe having protective shielding for preventing injury to persons by being pricked by the syringe after use. A shield is mounted to the sleeve for longitudinal movement, and this is extendable from a retracted position in which the shield is withdrawn from the syringe of the syringe, to an extended position in which the shield is positioned around the syringe so as to cover the tip portion thereof. The shield may be made up of first and second clamshell halves which are spread apart from one another along the sides of the tubular sleeve in the retracted position, and which come together in the extended position so that their tip portions cover the syringe. The shield may be extended manually by means of a button, or automatically by means of a spring mechanism. Disinfectant pads may be mounted to the interior surfaces of the clamshell halves so that these come into contact with the tip of the syringe and sterilize it when the clamshell halves are extended.

12 Claims, 5 Drawing Sheets

HYPODERMIC SYRINGE HAVING SHIELDING TO PREVENT ACCIDENTAL INJURY FOLLOWING USE

FIELD OF THE INVENTION

The present invention relates primarily to hypodermic syringes, and, more particularly, to a hypodermic syringe having shielding which extends to cover the point of the syringe after use so as to prevent accidental injury.

BACKGROUND OF THE INVENTION

Discarded hypodermic syringes present a serious health hazard. It is not unusual for people to be accidentally pricked by a syringe after use, and to so become infected with a disease transmitted from the person for whom the syringe was originally used. For example, personnel cleaning up hospital spaces or doctors' offices frequently must pick up numerous such syringes after use, and it is very easy to be accidentally stuck by the syringes when doing this. Furthermore, used hypodermic syringes frequently disposed of in plastic garbage bags, which are readily pierced by the syringes so that these are exposed and can easily prick a person who is handling the garbage. Also, municipal garbage is frequently dumped at sea, and there have been cases where syringes have washed up on the beach, where they may be stepped on by barefoot strollers. The seriousness of this problem has grown significantly with the spread of the Acquired Immune Deficiency Syndrome (AIDS) virus.

Some attempts have been made to eliminate the problem of accidental injury from used hypodermic syringes. For example, devices have been provided which cut or snap the metal syringe off from the plastic body of the syringe, both to prevent its re-use, and to also retain the severed syringe in a suitable, relatively thick-walled disposal container. While this provides a relatively satisfactory solution for many facilities, it is not without its drawbacks. For example, hospitals and many doctors' offices have a great many treatment rooms, and it is expensive and often simply not practical to install such a syringe clipping device in each of these rooms for the relatively occasional use which it will receive. More seriously, paramedics and other emergency response personnel who must administer injections at an accident or other emergency scene obviously cannot be burdened with carrying an additional piece of equipment in the form of a syringe clipper, and, in any event, they typically do not have time to use such a device; this problem is seriously aggravated at many accident sites, such as an automobile accident where the paramedic must work in a confined space or lie on the ground in a close proximity with the used hypodermic syringes, and so be at increased risk of accidental injury due to being pricked by one of these. A similar situation is faced by military medical personnel in combat situations, and also in military field hospitals.

Accordingly, there exists a need for a hypodermic syringe which provides for protection against injury due to persons being pricked by the needle after use, without requiring a separate device for doing this. Furthermore, there is a need for a syringe having such a provision which is inexpensive to manufacture and simple to operate.

SUMMARY OF THE INVENTION

The present invention has solved the problems cited above, and comprises generally a hypodermic syringe having extendable protective shielding for preventing injury due to the syringe pricking persons after it has been used. The syringe comprises a tubular sleeve having a hypodermic needle extending from its lower end. A plunger is positioned in the sleeve for injecting fluid from the sleeve through the needle. Shield means are mounted to the sleeve for longitudinal movement; means are provided for extending the shield means from a retracted position in which the shield means are withdrawn from the hypodermic needle so as to expose a tip portion thereof, to an extended position in which the shield means are positioned around the hypodermic needle so as to cover the tip portion thereof.

The shield means may comprise first and second clamshell halves which are spread apart from one another on opposite sides of the tubular sleeve when in the retracted position, and which are extended from the lower end of the tubular sleeve in the extended position so that the leading edge portions thereof cover the tip portion of the hypodermic needle.

The means for extending the shield means may be manually operable, or may be automatic. The manually operable means may comprise a button mounted to the upper end portions of the clamshell halves, this button having an end portion which is configured to be engaged by the finger of an operator so as to enable that operator to exert longitudinal force on the clamshell halves towards the extended position. A housing may enclose the clamshell halves in their retracted position, and this may have the longitudinally extending slot formed therein, through which the outer end of the button extends laterally, this slot being configured to permit longitudinal movement of the button therein as the clamshell halves are extended from the retracted position to the extended position. The housing may also be provided with a window portion for permitting viewing of capacity markings on the tubular sleeve within the housing.

Yieldable stop means may be provided for retaining the clamshell halves in the retracted position, these being configured to be overcome by the longitudinal force which is exerted by the operator, so as to permit the clamshell halves to be selectively extended to their extended position. This yieldable stop may be a restraining shoulder formed on the lower end of the tubular sleeve, this having a sloped upper surface which is configured to abut the leading edge of the clamshell halves so as to restrain these in the retracted position, and so that the leading edges of the clamshell halves ride over the restraining shoulder in response to the longitudinal force which is exerted thereon by the operator.

In those embodiments having automatic means for extending the clamshell halves, this may comprise means for biasing the clamshell halves from the retracted position towards the extended position, means for retaining the clamshell halves in the retracted position, and means for selectively releasing the clamshell halves from the retaining means so that the biasing means automatically extend the clamshell halves to the extended position. The biasing means may be at least one spring, and this may be a coil spring which is compressed between a fixed upper portion of the sleeve and an upper portion of the longitudinally movable clamshell halves so as to bias the clamshell halves towards the extended position. The coil spring may be positioned concentrically around the tubular sleeve of the syringe, with the upper end of the spring abutting an outwardly extending flange which is mounted about the sleeve, and the lower end abutting a thrust ring which is mounted to the upper ends of the clamshell halves and which is positioned concentrically around the tubular sleeve for longitudinal movement. The coil spring and the clamshell halves in the retracted position may be enclosed by housing which is mounted to the flange about the upper end of the sleeve, and which extends downwardly therefrom. The retaining means for embodiments having the automatic extension means may comprise a laterally extending shoulder mounted to a lower portion of the tubular sleeve, this shoulder having an upper surface which is configured to abut the leading edges of the clamshell halves so as to restrain these against the downward bias exerted by the biasing means. The means for selectively releasing the clamshell halves from the retaining means may comprise means for selectively forcing the leading edges of the clamshell halves off of the shoulder so that these freely slide over the shoulder, and this means may comprise an actuating rod which is mounted to an upper portion of the plunger and extends downwardly to a lower end which is configured to press the leading edge of the clamshell half laterally off of the retaining shoulder in response to depression of the plunger to a selected position. The tubular sleeve may be configured to eject its predetermined dosage of fluid in response to depression of the plunger to a first selected position, with the release means being configured to then release the clamshell halves in response to additional depression of the plunger from the first selected position to a second selected position. A yieldable stop may be provided for arresting of the plunger in the first selected position so as to enable the operator to withdraw the syringe of the syringe from the patient after injecting the predetermined quantity of fluid, this yieldable stop being configured so as to permit the plunger to be depressed past the first selected position to the second selected position (in which the clamshell halves are released) in response to selective manual application of pressure to the plunger.

The two clamshell halves may be inwardly flexible, so that in the extended position these flex inwardly to cover the tip portion of the syringe in response to manual pressing of the clamshell halves together. Means may be provided for locking the leading edge portions of the clamshell halves together in this position, and this locking means may be a male member mounted to the leading edge portion of the first clamshell half, and a female member mounted to the leading edge of the second clamshell half for lockingly engaging the male member as the leading edge portions of the clamshell halves are pressed together.

The hypodermic syringe may further comprise sterilizing means mounted interiorly to the shield means, with the sterilizing means being configured to be brought into contact with the tip portion of the syringe so as to sterilize this in response to extension of the shield means to its extended position. The sterilizing means may be first and second disinfect pads which are impregnated with a disinfectant material for sterilizing the hypodermic syringe, the pads being mounted to the interior surfaces of the clamshell halves so that in response to extension of the clamshell halves to the extended position, in which their leading edges cover the tip of the syringe, the first and second disinfectant pads are brought into contact with the tip of the syringe so as to sterilize this. The disinfectant pads may be formed of a resiliently compressible material which is partially compressed against the tubular sleeve when the clamshell halves are in the retracted position, and which expands so as to surround the tip portion of the syringe when the clamshell halves are in the extended position.

Objects and advantages of the invention not clear from the above will be understood by a reading of the detailed description of the invention and a review of the accompanying drawings.

DETAILED DESCRIPTION

Figure 1:
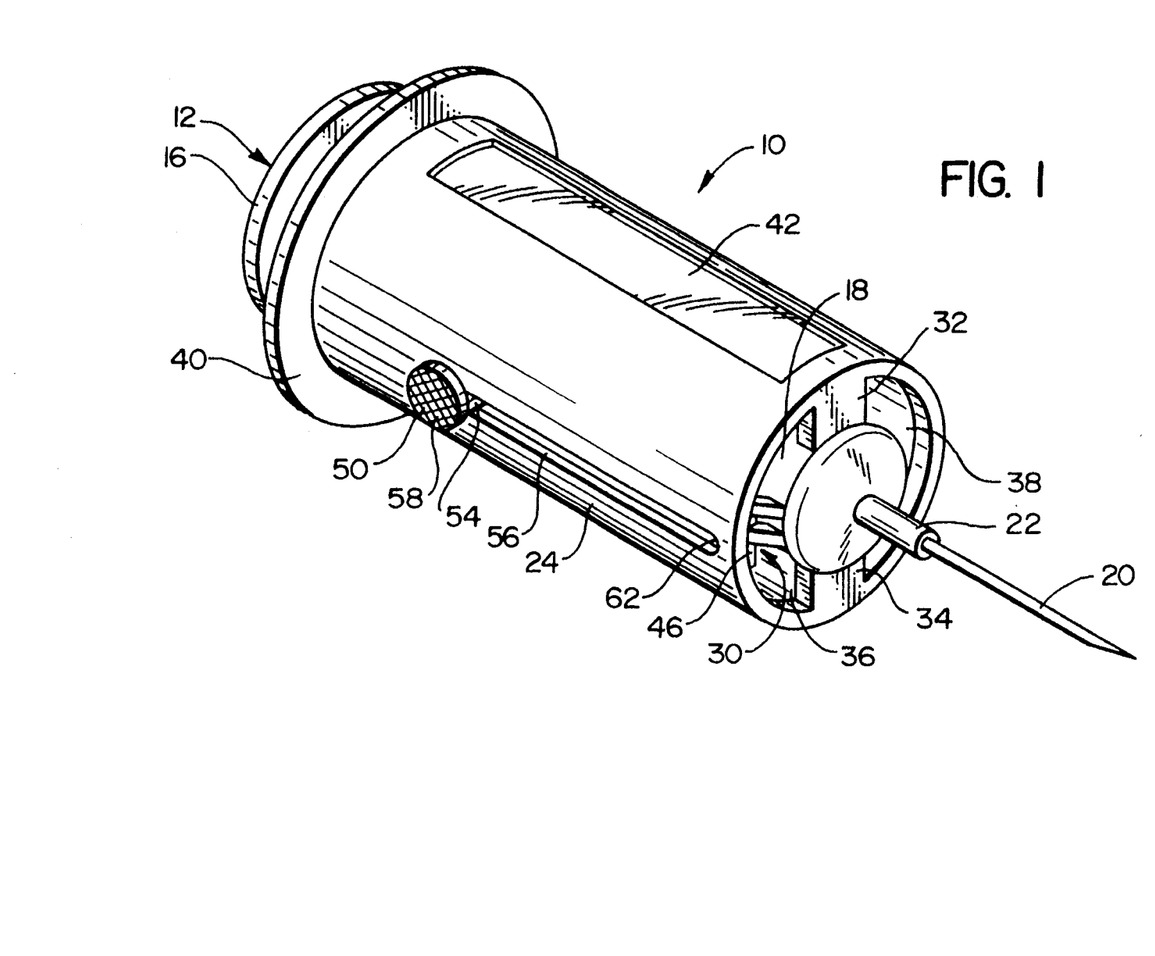
FIG. 1 is a perspective view of a hypodermic syringe incorporating the present invention, this having first and second clamshell halves which encases the needle of the syringe.

FIG. 1 shows a syringe 10 incorporating the present invention. This has a generally conventional central sleeve defining a bore, with a plunger assembly 12 being positioned in this to draw this fluid into the sleeve and then inject this fluid into the patient. Plunger assembly 12 has a central shaft portion 14 (which has a generally cruciform cross section in the particular syringe which is shown), with a planar head 16 being mounted on the upper end of this for manipulation by the operator.

At the other end of syringe 10 there is a generally conventional tubular metallic syringe 20 which is used to pierce the patient's skin, this being supported about its base by boss 22. This boss extends from the lower end or base of the tubular sleeve 18 of the syringe, there being a continuous passage 23 from the interior of this sleeve through the boss 22 and syringe 20.

A cylindrical housing 24 surrounds the sleeve portion 18 of syringe 10, and this encloses the protective shield assembly 30 when this is in its retracted position. The lower end of housing 24 (as used in this description and the appended claims, the term "lower" will refer to that end of the syringe which is directed towards the surface of the patient's body for injection, while the term "upper" will denote the opposite) is supported about central sleeve 18 by radially extending struts 32, 34; these leave first and second semi-circular openings 36, 38 in the end of housing 24, the purpose of which will become apparent from the following description. At the upper end of housing 24 there is a radially extending flange 40 which is configured to be gripped by the fingers of the operator so as to assist in the operation of the plunger assembly of the syringe. To provide a clear view of the capacity markings (not shown) on central sleeve 18, a clear, longitudinally extending window portion 42 is provided in the side of housing 24; alternatively, this window portion may be provided by a simple cut-away opening, or the entire housing may be made of a suitably transparent material.

Shield assembly 30 is made up of first and second clamshell halves 46, 48 (46 only being shown in FIG. 1). These are retained in the retracted position within housing 24 prior to use of the syringe. A radially (outwardly) extending button 15 is mounted to the upper end of these clamshell halves by means of a stem 54 which rides in a longitudinally extending slot 56 formed in the wall of housing 24. Button 50 has a knurled outer surface 58 which provides an enhanced grip for the finger of an operator. When button 50 is positioned in its upper position, near the upper end of slot 56 as shown in FIG. 1, the clamshell halves of shield assembly 30 which are attached thereto are retracted into housing 24. Then, to extend the clamshell halves, the operator engages the outer surface 58 of button 50 with a finger and slides this downwardly so that the stem 54 of the button slides downwardly through slot 56 towards its lower end 62; as this is done, the clamshell halves which are attached to the stem of the button extend downwardly out of housing 24 through the semi-circular openings 36, 38, generally parallel to syringe 20. As will be described in greater detail below, these then form a protective shield which covers the point of syringe 20 so as to prevent this from accidentally pricking a person. The first and second clamshell halves may be linked by a suitable connecting member (not shown in FIGS. 1-3, but shown in FIGS. 5-7) so that they extend simultaneously from the housing.

Figures 2, 3, 4:
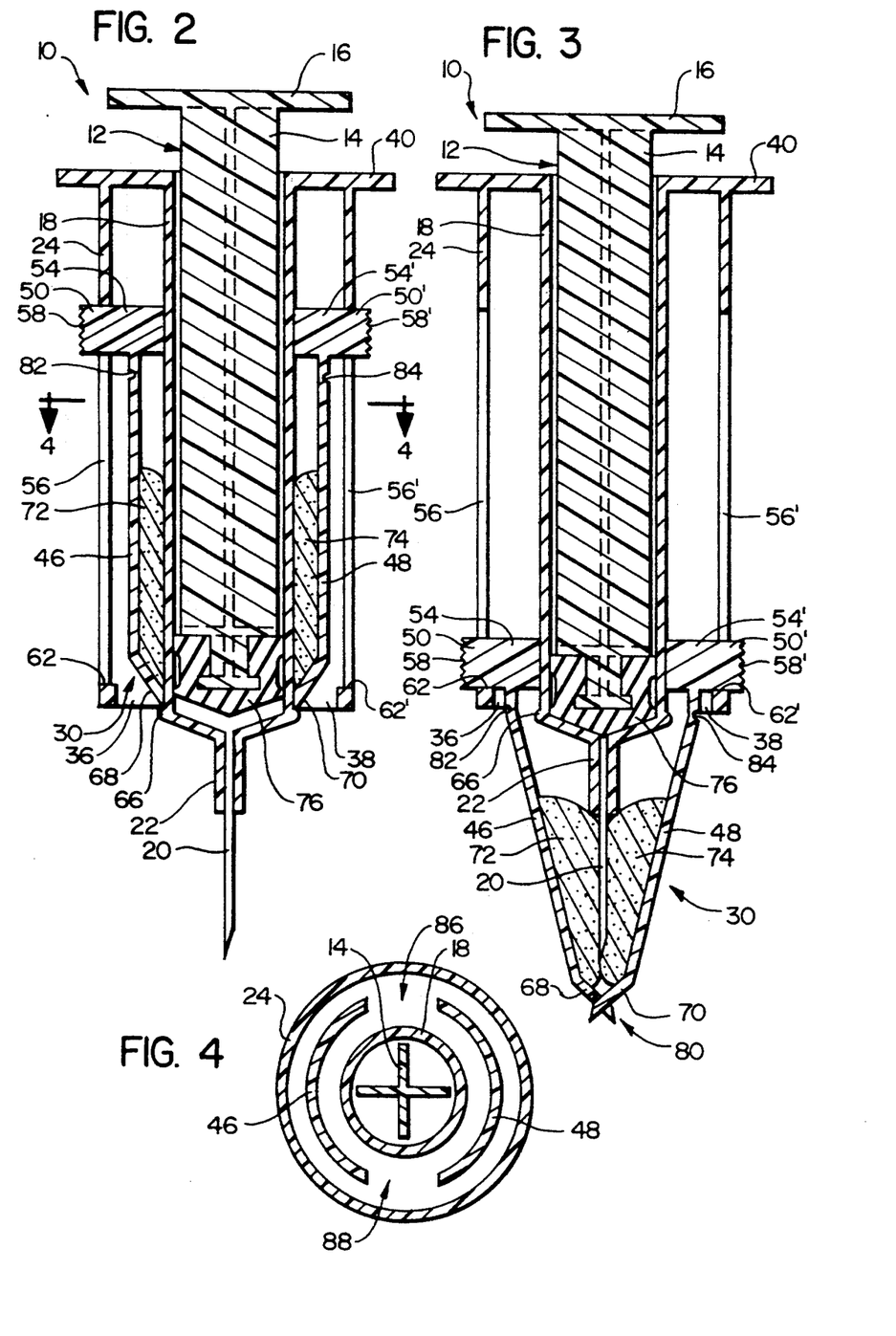
FIG. 2 is a longitudinal cross-sectional view of the syringe of FIG. 1, showing the protective clamshell halves in their retracted position.
FIG. 3 is a cross-sectional view similar to FIG. 2, showing the clamshell halves in extended and snapped together so as to form a protective shield which covers the point of the needle.
FIG. 4 is a transverse cross-sectional view taken along line 4—4 of FIG. 2, showing the concentric arrangement of the semi-cylindrical clamshell halves about the central sleeve of the syringe, and the surrounding outer housing.

FIGS. 2-3 in greater detail show how the shield assembly is extended from the housing and secured together. FIG. 2 shows the shield assembly 30 in its retracted position. As previously described, shield assembly 30 is made up of first and second clamshell halves 46, 48. In the embodiment illustrated in FIG. 2, there is a button 50, 50' mounted at the upper end of each of these clamshell halves, each of these buttons being provided with a knurled outer surface 58, 58'; this provides an arrangement where the two buttons can conveniently be grasped between the thumb and forefinger of the operator's hand, so as to achieve very positive and effective downward motion which extends the shield assembly.

Prior to its extension, shield assembly 30 is retained in the retracted position by a circumferential sloped shoulder 68 about the lower end of sleeve portion 18, which abuts the inwardly tapered leading edges 68, 70 of the two clamshell halves; when downward pressure is applied by the operator to the buttons 50, 50', this force causes the leading edges 68, 70 of the clamshell halves to ride up over the sloped retaining shoulder 66 so that the shield assembly can be extended.

Mounted to the inner surface of each of the clamshell halves 46, 48 of the shield assembly is a disinfectant pad 72, 74. As will be described in greater detail below, these come into contact with the syringe 20 when the shield assembly is extended so as to destroy any pathogens thereon.

FIG. 2 also shows how flange portion 40 extends inwardly from housing 24 to sleeve 18 so as to support these members relative to one another, with these pieces (sleeve 18, flange portion 40, and housing 24) being formed integrally with one another if desired. Furthermore, FIG. 2 shows the resilient seal member 76 which is mounted to the lower end of the shaft portion 14 of plunger assembly 12 so as to form a sliding seal against the inner wall of sleeve 18.

FIG. 3 shows the shield assembly 30 in its extended position, this having been achieved by pushing buttons 50, 50' to the lower end of the slots 56 in housing 24 in the manner previously described. As this is done, the two clamshell halves 46, 48 extend from housing 24 through openings 36, 38, respectively. The operator then grasps the two clamshell halves between his fingers and presses these together so that a locking mechanism 80 at the leading edges 68, 70 of the two clamshell halves (which will be described below with reference to FIGS. 5-7) engages so as to hold these together. The bending of the two clamshell halves together is facilitated by grooved hinge portions 82, 84 formed at their upper ends (proximate the stems 54, 54' of the buttons) so as to relatively weaken the clamshell halves at these points so that the material bends at this point.

Disinfectant pads 72, 74 are preferably formed of a suitable resiliently compressible material, such as polyurethane foam, rubber foam, etc., this being impregnated with a suitable antiseptic material. An eminently suitable and inexpensive material for this purpose may be dry, powdered bleach, this being activated by contact with residual moisture on syringe 20 and having been found effective at destroying the AIDS virus, amongst other pathogens. Preferably, the pads 72, 74 are partially compressed against the exterior of sleeve 18 when the clamshell halves are in the retracted position shown in FIG. 2, and so when the clamshell halves are extended from the housing, the resilient pads expand inwardly towards one another. Then, when the two clamshell halves of the shield assembly are bent towards one another and locked together as shown in FIG. 3, the resilient pads 72, 74 on their inner surfaces are forced against syringe 20 so as to ensure that effective contact is achieved therewith, ensuring that the disinfectant compound is effectively applied thereto. In this respect, it will be observed from FIG. 3 that the boss 22 about the base of syringe 20 serves not only to support syringe 20, but also ensures that the portion of syringe 20 which may have contacted the body of the patient during injection is extended somewhat away from the lower end of sleeve 18 so that contact is more readily achieved therewith by hands 72, 74 without requiring extreme inward angulation of the two clamshell halves, which might otherwise make it difficult to configure the clamshell halves so that they would also extend to cover the point of the syringe.

FIG. 4 shows the generally concentric arrangement of the sleeve 18, and the surrounding clamshell halves 46, 48 in housing 24. In particular, FIG. 4 shows the central sleeve 18 of the syringe, in which the shaft portion 14 of the plunger assembly is disposed. Housing 24 is mounted around the outside of sleeve 18 as previously described so to form an annular cavity between the sleeve and the housing. The first and second clamshell halves 46, 48 of the shield assembly are disposed in this annular cavity so that these may move longitudinally therethrough in response to longitudinal pressure being exerted on the finger buttons by an operator as previously described. As is seen in FIG. 4, the clamshell halves 46, 48 are generally semi-cylindrical in form, with the edges of these being spaced apart to form gaps 86, 88, which are sized to provide clearance for the struts 32, 34 at the lower end of the housing (see FIG. 1) as the clamshell halves move past these.

Figure 5:
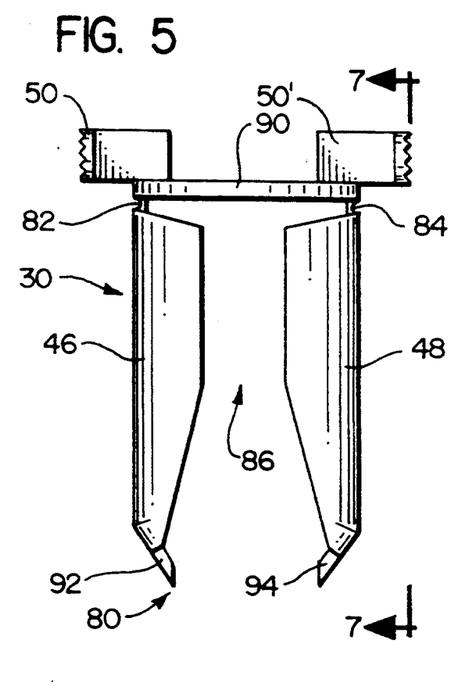
FIG. 5 is an elevational view of the clamshell halves of the syringe of FIGS. 1-4, showing these spread apart from one another in the configuration in which they initially extend from the outer housing of the syringe.
Figure 6:
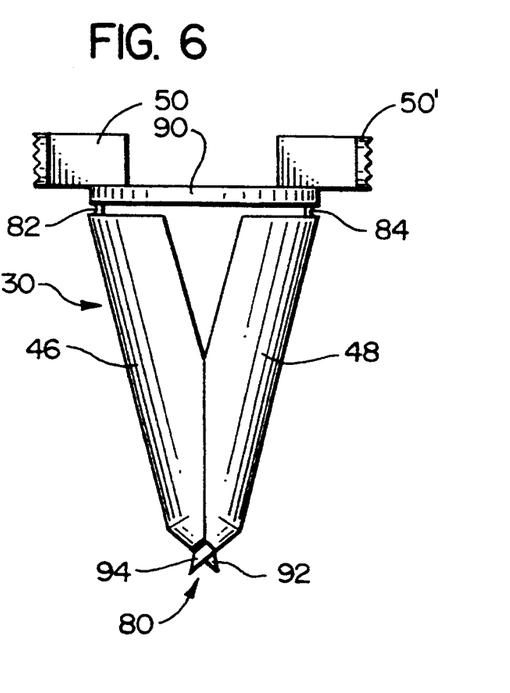
FIG. 6 is a view similar to that of FIG. 5, showing the clamshell halves having been pressed together so as to enclose the syringe of the syringe, and so that connector portions at the forward ends of the clamshell halves are snapped together into engagement to hold the clamshell halves closed.
Figure 7:
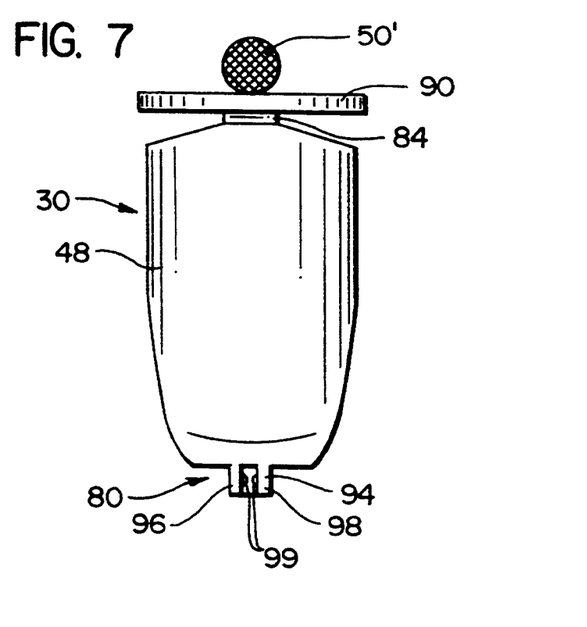
FIG. 7 is an elevational view of the shield assembly of FIG. 5, rotated 90° from the view shown in FIG. 5, showing one of the two clamshell halves.

FIGS. 5–7 show the components making up the shield assembly 30, and how the first and second clamshell halves 46, 48 bend together to form a shield about the syringe once these have been extended beyond the end of the housing 24. In particular, FIG. 5 shows the clamshell halves 46, 48 as they are configured in their retracted position, and then in their initially deployed position, these being spread apart so that they can extend through the openings 36, 38 at the end of housing 24 (see FIG. 1). FIG. 5 also illustrates one of the gaps 86 which is formed between the longitudinal edges of the clamshell halves to accommodate their passage around the support struts 32, 34 at the end of the housing. At their upper ends, clamshell halves 46, 48 are joined by the grooved hinged portions 82, 84 to a circumferentially extending support ring 90, which interconnects the two clamshell halves and ensures that they move together simultaneously as a unit. The operating buttons 50, 50' are also fixedly mounted to this support ring 90, so that the downward forces exerted by the operator are transmitted therethrough to the clamshell halves. Then, at the lower ends of clamshell halves 46, 8, there are male and female connector members 92, 94, respectively, which make up locking mechanism 80.

FIG. 6 shows the clamshell halves 46, 48 of shield assembly 30 having been pressed and snapped together in the configuration which is also shown in FIG. 3, so as to form the protective shield around the syringe of the syringe. As was noted above, to do this, the operator presses downwardly on the buttons 50, 50' to extend the clamshell halves and then presses these laterally together around the syringe. As this is done, the male and female portions 92, 94 of lock mechanism 80 move into engagement with one another so as to hold the clamshell halves together in the closed configuration. As shown in FIG. 7, the female connector member 94 may be a bipronged member having first and second lugs 96, 98, with these having inwardly projecting knobs 99 which engage the single lug of male member 92 as this passes between the two lugs of the female member. Of course, it will be recognized that this arrangement simply illustrates one of many possible arrangements for locking the two clamshell halves together.

At this point, it should also be noted that in some embodiments provisions may be made for bringing the first and second clamshell halves together into abutment with one another in the closed position, in addition to simply pressing these together in the manner which has been described above. For example, the outer walls of the openings 36, 38 in the end of the housing may be configured to slidingly abut the outer surface of the clamshell halves, so that as the hinge portions thereof are moved closer to these openings, the clamshell halves are angled towards one another so that their outer ends move into abutment. As another example, with some materials it may be possible to use the memory of the material to achieve the desired closed position; in other words, the clamshell halves may be molded to have the memory of the closed position and then moved to the retracted position, so that when they are subsequently extended from the housing, they are returned to the closed configuration by the memory of the material.

FIGS. 8–11 illustrate a second embodiment of the invention, wherein the clamshell halves, rather than being extended by direct manual manipulation in the manner described above, are selectively released by operation of the plunger assembly so that they are automatically spring-biased to their extended position. Inasmuch as numerous members (e.g., sleeve 18, plunger assembly 12, housing 24) are shared by this embodiment and that which has been previously described, like reference numerals will refer to like elements in FIGS. 1–7 and FIGS. 8–11.

Figure 8:
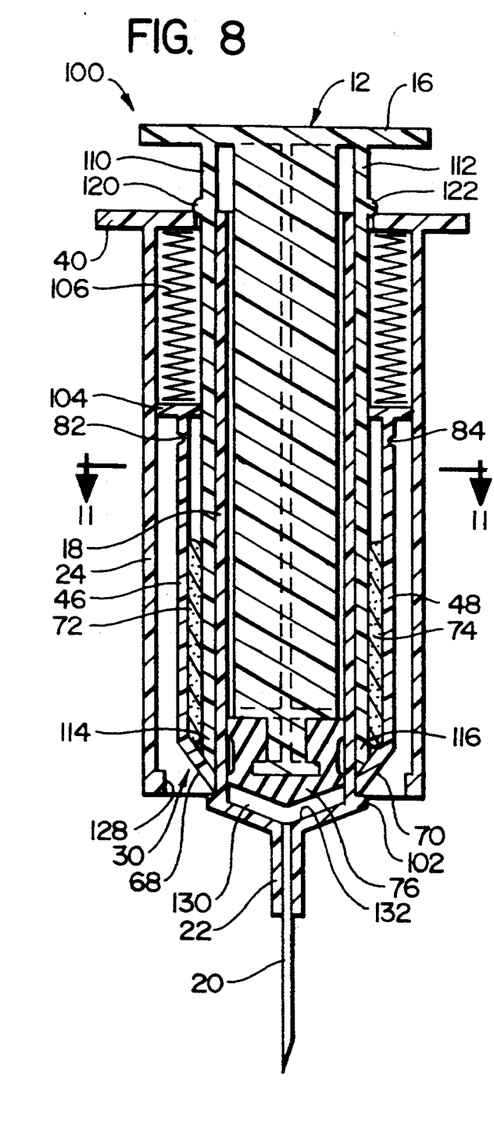
FIG. 8 is a longitudinal cross-sectional view similar to that of FIG. 2, showing a syringe which incorporates a second embodiment of the present invention, this having a spring-loaded shield assembly which is released by depression of the plunger of the syringe.

FIG. 8 shows the clamshell halves 46, 48 of shield assembly 30 in their retracted position; however, in this embodiment, the retaining shoulder 102 about the end of sleeve 18 is perpendicular rather than sloped, so that this abuts the leading edges 68, 70 of the clamshell halves so as to hold these in place against a downward force or bias tending to extend the shield assembly, until these are positively released from the retaining shoulder.

At the upper end of the clamshell halves, the outwardly extending buttons of the embodiment discussed above are replaced by a generally planar thrust ring 104 which fits generally around sleeve 18 and within housing 24 for vertical movement therein. A spring 106 is positioned between thrust ring 104 and the upper flange 40 of housing 24 so as to bias thrust ring 104 in a downward direction. Preferably, this may be a single coil spring wound concentrically around sleeve 18; however, a plurality of springs or other biasing members may be substituted for this. Because spring 106 tends to bias thrust ring 104 downwardly, it tends to bias the clamshell halves of shield assembly 30 towards their extended position; however, as noted above, these are restrained against such movement by retaining shoulder 102 until positively released from engagement therewith.

Release of the clamshell halves from their engagement with retaining shoulder 102 is accomplished by means of first and second actuating rods 110, 112, which extend downwardly from the head portion of the plunger assembly and along the sides of sleeve 18 to lower ends 114, 116. First and second stops 120, 122 are formed on actuating rods 110, 112 near the upper ends thereof. These stops react against flange 40 at the upper end of housing 24 so as to arrest the downward motion of plunger assembly 12 once the correct amount of fluid has been injected, so as to permit the syringe 100 to withdraw from the patient prior to extending the shield assembly. In this position, the lower ends 114, 116 of the actuating rods are positioned in abutment with the inner surfaces of the tapered leading edges 68, 70 of clamshell halves 46, 48.

Figure 9:
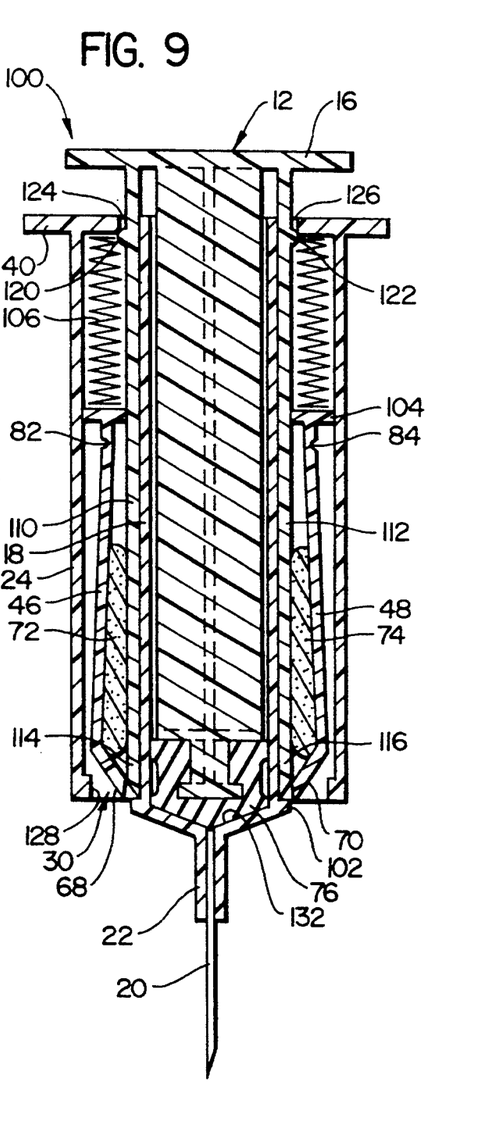
FIG. 9 is a view similar to FIG. 8, showing the plunger having been depressed past a set of stops so as to release the clamshell halves of the shield assembly from a retaining shoulder.

As is shown in FIG. 9, additional depression of plunger assembly 12 forces stops 120, 122 to deform slightly and to pass through passages 124, 126 in flange 40; the force required to accomplish this is not excessive, but is sufficient to prevent an operator from accidentally depressing the plunger assembly to this position before the syringe has been withdrawn from the patient's body. As plunger assembly 12 is depressed past the first stop position shown in FIG. 8 to the second stop position shown in FIG. 9, the outwardly bevelled lower ends 114, 116 of the actuating rods 110, 112 react against the inner surfaces of the leading edge portions 68, 70 of clamshell halves 46, 48, forcing the leading edges of the clamshell halves to flex outwardly, this flexing motion being facilitated by grooved hinged portions 82, 84. As this is done, the leading edges 68, 70 of the clamshell halves move outwardly beyond the radial limit of retaining shoulder 102, and are so released therefrom.

Figure 10:
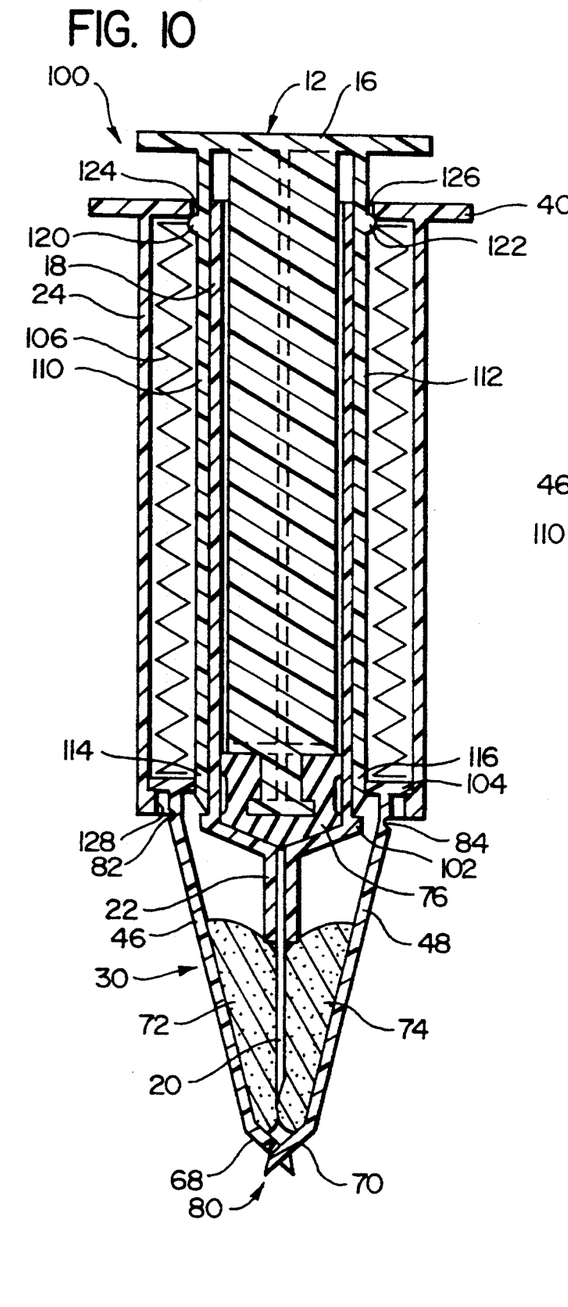
FIG. 10 is a view similar to FIGS. 8-9, showing the shield assembly having been automatically extended from the end of the housing of the syringe by the spring, and the clamshell halves then having been snapped together so as to enclose the syringe.

Then, as is shown in FIG. 10, the clamshell halves of the shield assembly are automatically extended from the lower end of housing 24 by the bias exerted by spring 106, until the downward motion of the clamshell halves is arrested by the abutment of thrust ring 104 against an inwardly extending shoulder 128 formed about the lower end of housing 24. The clamshell halves can then be pressed together and locked in the manner previously described so as to form a shield about the syringe 20 of syringe 100.

It will be appreciated from a review of FIGS. 8 and 9 that a small amount of fluid will remain in syringe leg in cavity 130 when the stops 120, 122 halt the motion of plunger assembly 12 in its first position shown in FIG. 8 and the syringe is withdrawn from the patient. This fluid will then be discarded when the plunger assembly is depressed to its second stop position as shown in FIG. 9. In general, this wastage will be negligible, and the capacity markings on the syringe can be adjusted to compensate for this. However, it will be understood that it may be desirable to eliminate this wastage, as, for example, by forming seal member 76 so that this is deformable longitudinally after it has abutted the end 132 of sleeve 18; in other words, the seal member 76 may be configured to abut the end 132 of sleeve 18 when the stops 120, 122 first arrest the motion of plunger assembly 12 in the position shown in FIG. 8, so that substantially all of the fluid is ejected from the syringe 100, and then this seal member 76 may deform longitudinally so as to permit the head and shaft portions of the plunger assembly to be depressed further to the second position shown in FIG. 9 so that the lower ends of the actuating rods cause the leading edges of the clamshell halves to be released from retaining shoulder 102. It will be appreciated, of course, that other release mechanisms may be substituted for those which have been described above; for example, the shield assembly may be positively retained by pins or the like which are cut or sheared by the lower ends of the actuating rods as the plunger is depressed. Alternatively, the syringe may be configured to have other release mechanisms that which do not require actuation by plunger assembly being moved from first to second positions at the end of its stroke.

Figure 11:
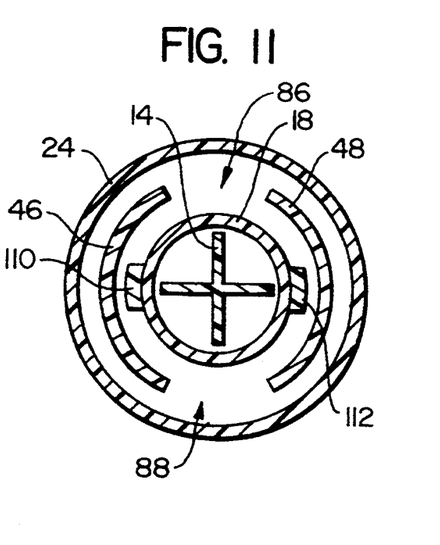
FIG. 11 is a transverse cross-sectional view taken along line 11—11 of FIG. 8, showing the arrangement of the retracted clamshell halves about the central sleeve of the syringe, and the surrounding housing.

FIG. 11 shows a transverse cross section taken through syringe 100. In general, this shows a concentric construction substantially similar to that shown in FIG. 4, with the exception that FIG. 11 shows the first and second actuating rods 110, 112 and how these extend along the sides of inner sleeve 18.

Having described the invention in its preferred embodiments, it will be clear that many changes and modifications may be made without departing from the spirit of the invention. It is therefore not intended that the words used to describe the invention or the drawings illustrating the same be limiting on the invention. Rather, it is intended that the invention only be limited by the scope of the appended claims.

What is claimed is:

1. A hypodermic syringe having protective shielding for preventing injury due to pricking of persons after use, said syringe comprising:

a tubular sleeve;

a hypodermic syringe in fluid communication with said sleeve and extending longitudinally from a lower end thereof;

a plunger positioned for longitudinal movement in said tubular sleeve for injecting fluid from said sleeve through said syringe;

shield means mounted to said sleeve for longitudinal movement, said shield means comprising first and second clamshell halves, said clamshell halves being spread apart from one another on opposite sides of said tubular sleeve in a retracted position, and being extended from said lower end of said tubular sleeve in an extended position so that leading edge portions of said clamshell halves cover a tip portion of said syringe; and manually operable means for extending said shield means from said retracted position, in which said shield means is withdrawn from said hypodermic syringe so as to expose a tip portion thereof, to said extended position, in which said shield means is positioned around said hypodermic syringe so as to cover said tip portion thereof;

said manually operable means for extending said clamshell halves comprising button means mounted to upper end portions of said clamshell halves, said button means having at least one end portion which is configured to be engaged by a finger of an operator so as to enable said operator to exert longitudinal force on said clamshell halves towards said extended position.

2. The hypodermic syringe of claim 1, further comprising a housing for enclosing said clamshell halves in said retracted position.

3. The hypodermic syringe of claim 2, wherein said housing has at least one longitudinally extending slot through which said outer end of said button means extends laterally, said slot being configured to permit longitudinal movement of said button means therein as said clamshell halves which are mounted to said button means are extended from said retracted position to said extended position.

4. The hypodermic syringe of claim 3, wherein said housing further comprises a window portion for permitting viewing of capacity markings on said tubular sleeve within said housing.

5. The hypodermic syringe of claim 3, further comprising yieldable stop means for retaining said clamshell halves in said retracted position, said yieldable stop means being configured to be overcome by said longitudinal force exerted by said operator so as to permit said clamshell halves to be selectively extended to said extended position.

6. The hypodermic syringe of claim 5, wherein said yieldable stop means comprises a restraining shoulder formed on said lower end of said tubular sleeve, said restraining shoulder having a sloped upper surface which is configured to abut a said leading edge of a said clamshell half so as to restrain said clamshell half in said retracted position, and so that said leading edge of said clamshell half rides over said restraining shoulder in response to said longitudinal force exerted by said operator.

7. The hypodermic syringe of claim 1, wherein said first and second clamshell halves are inwardly flexible so that in said extended position said clamshell halves flex inwardly to cover said tip portion of said syringe in response to manual pressing of said clamshell halves together.

8. The hypodermic syringe of claim 7, further comprising means for locking said leading edge portions of said clamshell halves together in said extended position.

9. The hypodermic syringe of claim 8, wherein said locking means comprises a male member mounted to said leading edge portion of said first clamshell half, and a female member mounted to said leading edge portion of said second clamshell half for lockingly engaging said male member as said leading edge portions of said clamshell halves are pressed together.

10. The hypodermic syringe of claim 1, further comprising sterilizing means mounted interiorly to said shield means and configured to be brought into contact with said tip portion of said syringe so as to sterilize said tip portion in response to extension of said shield means to said extended position.

11. The hypodermic syringe of claim 1, further comprising first and second antiseptic pads impregnated with an antiseptic material for sterilizing said hypodermic syringe, said first pad being mounted to an interior surface of said first clamshell half and said second pad being mounted to an interior surface of said second clamshell half, so that in response to extension of said clamshell halves to said extended position in which said leading edge portions cover said tip portion of said syringe, said first and second antiseptic pads are brought into contact with said tip portion of said syringe so as to sterilize said tip portion.

12. The hypodermic syringe of claim 11, wherein said antiseptic pads are formed of a resiliently compressible material which is partially compressed against said tubular sleeve when said clamshell halves are in said retracted position, and which expands so as to substantially surround said tip portion of said syringe when said clamshell halves are in said extended portion.

* * * * *